(12) United States Patent
Jensen et al.

(10) Patent No.: US 9,211,988 B2
(45) Date of Patent: Dec. 15, 2015

(54) PACKAGING FOR GUMMY SUBSTRATUM

(75) Inventors: Steven D. Jensen, South Jordan, UT (US); Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 0 days.

(21) Appl. No.: 12/885,729

(22) Filed: Sep. 20, 2010

(65) Prior Publication Data

US 2011/0068019 A1   Mar. 24, 2011

Related U.S. Application Data

(60) Provisional application No. 61/276,993, filed on Sep. 18, 2009, provisional application No. 61/319,124, filed on Mar. 30, 2010.

(51) Int. Cl.

| | | |
|---|---|---|
| A61C 19/02 | (2006.01) | |
| B65D 75/32 | (2006.01) | |
| B65D 25/10 | (2006.01) | |
| B65D 75/30 | (2006.01) | |
| B65D 33/25 | (2006.01) | |
| B65D 75/36 | (2006.01) | |

(52) U.S. Cl.
CPC .............. *B65D 75/327* (2013.01); *B65D 25/10* (2013.01); *B65D 33/2508* (2013.01); *B65D 75/30* (2013.01); *B65D 75/367* (2013.01); *A61C 2202/00* (2013.01)

(58) Field of Classification Search
CPC .. A61C 19/02; A61C 19/066; A61C 2202/00; B65D 75/36; B65D 75/366; B65D 75/367; B65D 71/0085; B65B 5/04

USPC ......... 206/447, 460, 461, 472, 565, 564, 558, 206/63.5
See application file for complete search history.

(56) References Cited

U.S. PATENT DOCUMENTS

| | | | | | |
|---|---|---|---|---|---|
| 3,999,661 | A | * | 12/1976 | Jones | 206/591 |
| 4,183,446 | A | * | 1/1980 | Davis | 220/4.23 |
| 4,197,947 | A | * | 4/1980 | Zaidi | 206/438 |
| 4,844,251 | A | * | 7/1989 | Gueret | 206/222 |
| 5,203,143 | A | * | 4/1993 | Gutentag | 53/452 |
| 5,323,787 | A | * | 6/1994 | Pratt | 128/862 |
| 5,350,059 | A | * | 9/1994 | Chester et al. | 206/63.5 |
| 5,863,202 | A | * | 1/1999 | Fontenot et al. | 433/215 |
| 5,887,717 | A | * | 3/1999 | Anderson et al. | 206/460 |
| 5,911,319 | A | * | 6/1999 | Porcelli et al. | 206/63.5 |

(Continued)

OTHER PUBLICATIONS

English Translation of Office Action issued in Chinese Patent Application No. 201080041697.7 (PCT Application Entry into the National Phase) on Nov. 11, 2013.

*Primary Examiner* — Steven A. Reynolds
(74) *Attorney, Agent, or Firm* — CAO Group, Inc.

(57) ABSTRACT

Implementations of the present invention include methods, devices, and systems that provide effective packaging items with at least one gummy surface. In particular, implementations of the present invention provide a package for items with a gummy surface that does not require a separate liner to be placed on the gummy surface. In example implementations, the package includes inadhesive polymers such that the item can be removeably adhered to a portion of the package. Moreover, example embodiments of the present invention provide packaging devices, systems, and methods that allow an item with a gummy surface to be packaged without any part of the package interfacing with the gummy surface.

13 Claims, 4 Drawing Sheets

(56) References Cited

U.S. PATENT DOCUMENTS

| | | | |
|---|---|---|---|
| 5,947,278 A * | 9/1999 | Sawhney et al. | 206/216 |
| 5,950,830 A * | 9/1999 | Trigger | 206/440 |
| 6,168,026 B1 * | 1/2001 | Haggard et al. | 206/714 |
| 6,287,120 B1 * | 9/2001 | Wiesel | 433/215 |
| 6,357,594 B1 * | 3/2002 | Gutentag | 206/714 |
| 6,506,053 B2 * | 1/2003 | Wiesel | 433/215 |
| 6,568,535 B1 * | 5/2003 | Pylant | 206/713 |
| 6,860,736 B2 * | 3/2005 | Allred et al. | 433/80 |
| 6,997,708 B2 * | 2/2006 | Allred et al. | 433/80 |
| 7,568,579 B2 * | 8/2009 | Moore | 206/368 |
| 7,798,324 B2 * | 9/2010 | Wojcik | 206/372 |
| 7,967,145 B2 * | 6/2011 | Tchouangang | 206/570 |
| 2003/0211056 A1 * | 11/2003 | Sagel et al. | 424/53 |
| 2004/0146222 A1 | 7/2004 | Kinigakis et al. | |
| 2005/0186539 A1 * | 8/2005 | McLean et al. | 433/215 |
| 2005/0276760 A1 * | 12/2005 | Lokken | 424/53 |
| 2007/0114139 A1 * | 5/2007 | Moore | 206/63.5 |
| 2008/0011636 A1 * | 1/2008 | St. John et al. | 206/449 |
| 2008/0050693 A1 * | 2/2008 | Fischer et al. | 433/25 |
| 2008/0063325 A1 | 3/2008 | Miller et al. | |

* cited by examiner

PACKAGING FOR GUMMY SUBSTRATUM

CROSS-REFERENCE TO RELATED APPLICATIONS

This application claims the benefit of U.S. Provisional Application No. 61/276,993, filed Sep. 18, 2009, and U.S. Provisional Application No. 61/319,124, filed Mar. 30, 2010. Both the '993 and the '124 applications are incorporated herein by reference in their entirety.

TECHNICAL FIELD OF THE INVENTION

The present disclosure generally relates to packaging, and particularly to packaging of items having a sticky or tacky surface on at least a portion of a surface of the item (e.g., gummy substratum).

BACKGROUND OF THE INVENTION

Many items and products that are manufactured today are packaged for shipment to various commercial destinations. In fact, most products sold in today's economy are at one time or another packaged during the various stages of manufacturing, handling or shipping. Although there are various reasons for packaging a product (e.g., customer recognition or marketing) a primary purpose of a package is to protect the contents of the package during the handling and shipping process until the package is eventually opened by the end-user. Therefore, manufacturers often design packages to allow a particular product to arrive to the end-user in essentially the same condition as the product left the manufacturer.

Accordingly, packaging plays an important role for manufacturers of products to provide end-users with a quality product. Due to the importance of packaging, a manufacturer may scrutinize each individual item to determine the best and most efficient way to ship the item. Packaging and shipping expenses may be a costly and resource intensive portion of a manufacturer's production process. Any improvements in the packaging characteristics of an item that reduces the number of packages, the size of the package, and/or the time associated with packaging the item may greatly decreases the overall production cost of that particular item. Therefore, reducing packaging and shipping costs may be beneficial to a manufacturer, allowing for either increased profit or a more competitive price of the item in the market.

The successful packaging of varying types of items may present a varying set of packaging challenges, depending on the characteristics of the items to be packaged. For example, the following list represents various item categories and generally illustrates that the characteristics of an item to be packaged may be associated with the characteristics of the packaging of that item. Some example item categories may include:

1. Non-fragile solids—non-fragile solid items may be packaged in a plastic wrap or bag, and then placed in a box with standard cushioning material;
2. Fragile solids—fragile solid items may be packaged in a plastic wrap or bag, and then placed in a box with maximum amount of cushioning material;
3. Liquids—liquids may be packaged in a shatter-resistant container that is covered by a plastic wrap or bag; and
4. Gases—gases may be packaged in a metal puncture resistant cylinder that is covered in plastic wrap or a bag.

Notwithstanding the above general categories, some specialty items are much more difficult to package and ship, which often leads to customized packaging to allow adequate delivery of the specialty items to the end-user.

One example of specialty items that pose a packaging challenge may include substances and/or compounds that are gummy or sticky. Items that are gummy or sticky have an inherent property of adhering to items with which they come into contact. In particular, gummy or sticky items may adhere to conventional packaging or wrappers and, in most cases, make it nearly impossible to separate the item from the packaging. Thus, gummy or sticky items require customized packaging in order to successfully provide the gummy or sticky item to the end user.

Various strategies have been developed to manage the problems associated with packaging gummy or sticky items. Some convention strategies in packaging gummy or sticky items include:

1. No-stick wrapper—A no-stick wrapper may be a single component material designed at the molecular level to minimize adhesion between the gummy item and the wrapper. Examples of suitable no-stick wrapper materials include fluorinated or chlorinated polymers such as Teflon, polymeric silicone or PVC. Other materials could include solid waxes, such as paraffin.
2. Release Agents—Conventionally, release agents are compounds that are applied onto the packaging that minimizes adhesion between the gummy or sticky item and the packaging. Examples of release agents include waxes, such as those found coated onto wax paper. Other release agents could include oils, such as silicone or vegetable oils. Traditionally, oils may be applied on a polymeric or paper sheet.

Currently, there are various gummy or sticky items that are commercially available that utilize the various packaging techniques to package a gummy or sticky item. For example, a FRUIT ROLL-UP utilizes a type of no-stick wrapper. In particular, a FRUIT ROLL-UP is made of a thin sticky layer of a fruit laden confection that is applied to a sheet of cellophane. After application, the sheet of cellophane is rolled up such that both the front and back of the cellophane act as a continuous wrapper.

Although the packaging of the FRUIT ROLL-UP may protect both sides of the sticky fruit laden confection, this type of packaging has several disadvantages. One example drawback is that the ease of separating the confection depends on which side of the cellophane the confection releases first. Ideally the fruit laden confection releases on the leading end of the cellophane causing the roll to unravel and provide access to the FRUIT ROLL-UP. Often times, however, the fruit laden confection will stay stuck to the body of the roll causing the end-user to have to tediously and carefully peel away the confection. Furthermore, during the tedious peeling away process, the FRUIT ROLL-UP will often tear, causing the unpacking process to become increasingly more difficult and frustrating for the end-user.

Another disadvantage of a FRUIT ROLL-UP type wrapper is that it requires an additional package to environmentally seal the FRUIT ROLL-UP. In particular, a FRUIT ROLL-UP requires a no-stick wrapper to manage the sticky confection, and requires an additional package to environmentally seal the FRUIT ROLL-UP. Without the use of an additional package, the no-stick wrapper may fail to seal the FRUIT ROLL-UP, causing the FRUIT ROLL-UP to dry out and/or become contaminated.

An example of using a release agent in the packaging of gummy or sticky items is the packaging of salt-water taffy. The conventional wrapper for salt-water taffy is wax paper. The wax serves as a releasing agent because the wax is inherently harder to adhere to than paper. One disadvantage to using a release agent like wax is that the wax may release onto the candy and be ingested by the end user. Another disadvantage to the packaging design of saltwater taffy is that it is not individually environmentally sealed.

A third example of packaging a gummy or sticky item is dental whitening strips, such as CREST WHITESTRIPS. CREST WHITESTRIPS essentially consist of a plastic backing material layered with a coat of whitening gel that has a sticky characteristic. In order to protect the whitening gel, a release liner is used to cover the whitening gel. Thus, the whitening gel is positioned between a backing material and a release liner. The whitening gel is then placed within an additional package to protect the whitening gel from the environment, thus preventing the whitening gel from drying out or becoming contaminated.

One disadvantage to conventional packaging for whitening gels, as described above, is that if whitening gel is packaged without a release liner, then the whitening gel causes a mess and will not arrive to the end-user in a useable form. On the other hand, by using a release liner, an additional manufacturing step, as well as additional packaging material, is added to the packaging of the whitening gel, causing the cost to package and ship the whitening gel to increase. Moreover, a release liner does not seal out the sides of the whitening gel, and therefore a second environment package must be used, again causing the cost of packaging and shipping to increase.

Accordingly, there are a number of disadvantages in the conventional art of packaging gummy or sticky substances.

SUMMARY OF THE INVENTION

Implementations of the present invention include methods, devices, and systems that provide effective packaging items with at least one gummy surface. In particular, implementations of the present invention provide a package for items with a gummy surface that does not require a separate liner to be placed on the gummy surface. In example implementations, the package includes inadhesive polymers such that the item can be removeably adhered to a portion of the package. Moreover, example embodiments of the present invention provide packaging devices, systems, and methods that allow an item with a gummy surface to be packaged without any part of the package interfacing with the gummy surface (e.g., the gummy surface is suspended without contact from any part of the package).

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific example implementations thereof which are illustrated in the appended drawings. Understanding that these drawings depict only typical implementations of the invention and are not therefore to be considered to be limiting of its scope, the invention will be described and explained with additional specificity and detail through the use of the accompanying drawings in which.

DETAILED DESCRIPTION OF THE INVENTION

Figure 1A:
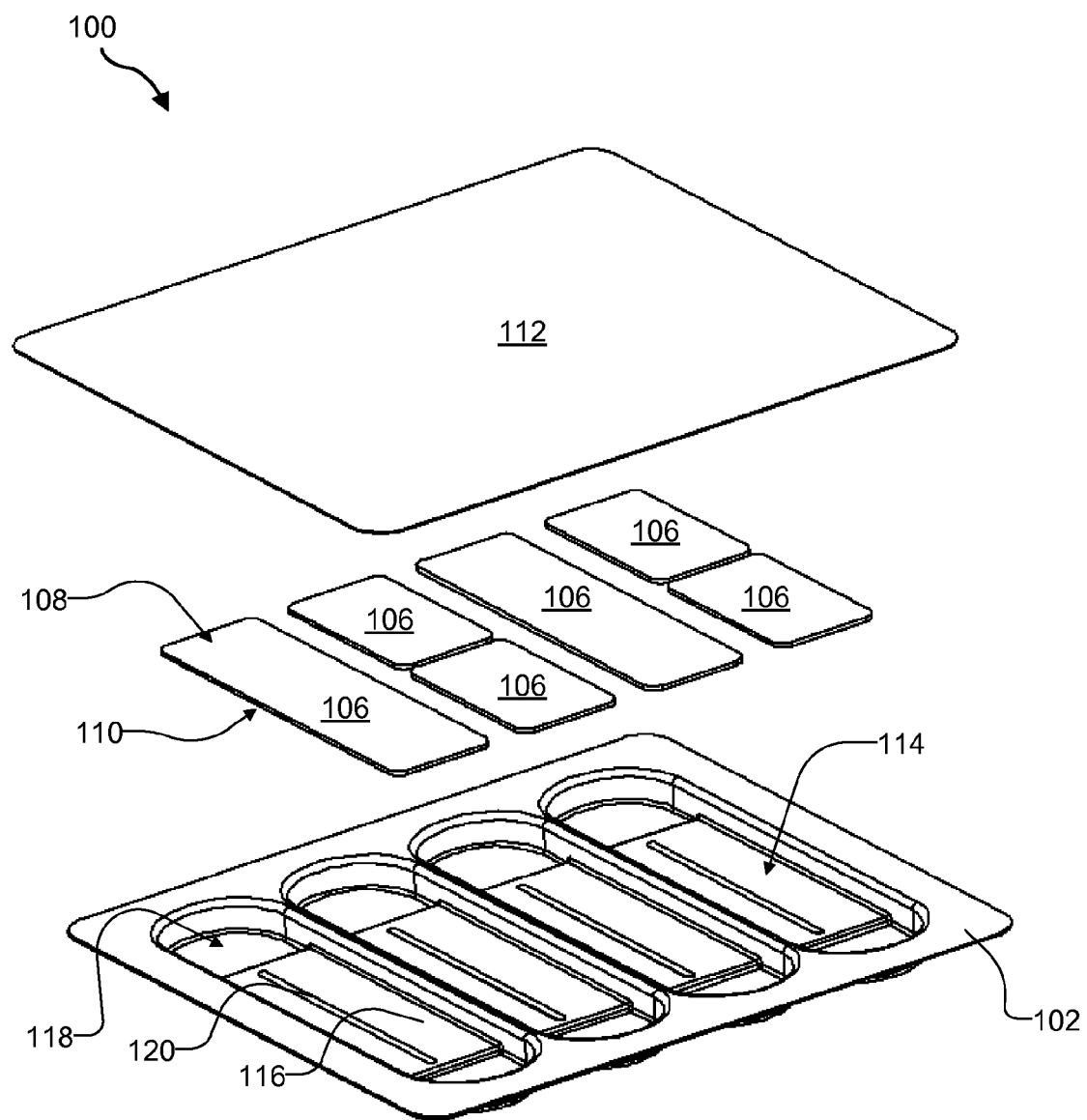
FIG. 1A illustrates an exploded view of a package according to principles described herein.

Implementations of the present invention include methods, devices, and systems that provide effective packaging items with at least one gummy surface. In particular, implementations of the present invention provide a package for items with a gummy surface that does not require a separate liner to be placed on the gummy surface. In example implementations, the package includes inadhesive polymers such that the item can be removeably adhered to a portion of the package. Moreover, example embodiments of the present invention provide packaging devices, systems, and methods that allow an item with a gummy surface to be packaged without any part of the package interfacing with the gummy surface (e.g., the gummy surface is suspended without contact from any part of the package).

As will be appreciated more fully herein, embodiments of the present invention provide an effective package for items having at least one gummy surface. In particular, example embodiments of the invention provide an environmentally sealed package that does not allow the item's gummy surface to dry out. Moreover, due to the sealed package, the item, and the gummy surface on the item, is protected from any contamination from outside the package.

Additionally, example embodiments of the present invention allow an end-user to easily open the package. Once opened, the package provides the user with easy access to the item with the gummy surface. Thus, although the item is gummy and sticky, the package allows an end-user to easily access the item for use without necessarily having to interfere with the gummy surface of the item.

Also, example embodiments of the present invention provide a cost effective and time efficient method of packaging items having at least one gummy surface. For example, the item with the gummy surface may be placed within the package without the need for a release liner, or similar device, to interface with the gummy surface. Thus, the present invention provides a package that requires less material and less time to package, which in turn reduces expenses.

In particular, the present invention contemplates the use of packaging that is more rigid than a thin sheet of plastic (e.g., plastic bag). Example embodiments include any environmentally sealable package that can maintain any given shape. For example, a relatively rigid plastic flat U-shaped, or V-shaped trough can be formed within the package, wherein the item with the gummy surface is positioned within the trough surface side-up. Due to the fact that the gummy surface is positioned within the trough with the gummy surface side-up, the gummy surface of the item never comes into contact with any packaging surface. The package is sealed with a cover that is sealed (e.g., attached, closed, bonded, or snapped) together to form an environmental seal.

As an overview, one example package according to the present invention includes a rigid plastic tray having one or more troughs formed into the rigid plastic tray. The item with the gummy surface may correspond to the shape of the troughs such that the item may fit snuggly or loosely into the trough. A thin bead of adhesive may be applied between the trough and the surface opposite the gummy surface on the item (backing material side). The adhesive bead temporarily holds the item in place within the trough. Finally, a cover may be sealed over the trough to environmentally seal the item within. In this manner, the package provides a confined free space around the gummy surface of the item wherein the gummy surface does not come into contact with anything until an end-user opens the package to access the item.

The various components of the package discussed above may be made of various materials. Conventional plastics such as polypropylene, PVC, polyethylene, and many other plastics are suitable as long as the required rigidity of the container is maintained.

In addition to the various materials with which the packaging can be made, the packaging can be configured to have any geometric dimension and configuration. As will be discussed further below, exemplary embodiments of the invention are directed toward packaging one or more treatment strips (e.g., dental treatment strips). Accordingly, the packaging described and illustrated below includes a substantially flat rectangular geometric configuration having dimensions that correspond to the relative dimensions of the dental treatment strips. However, the invention is not limited to these geometric configurations as the packaging can include almost any geometric configuration necessary for a particular item to be packaged.

Moreover, example embodiments of the present invention are not limited to packaging treatment strips. Rather, example embodiments of the present invention may be used to package almost any item that includes at least one gummy surface. For the purposes of this application, a gummy surface is a surface that includes one or more of the following properties: sticky, gel-like, jelly-like, gluey, and/or includes any adhesive characteristics.

Referring now to the drawings, FIG. 1A illustrates one example embodiment of a package 100 used to package items with a gummy surface. As briefly discussed above, the package 100 includes a rigid tray 102 that includes one or more troughs. For example, FIG. 1A illustrates that the rigid tray 102 can include four troughs 114. However, in alternative embodiments, the rigid tray 102 can include any number of troughs 114.

Each of the troughs 114 are designed to support and protect a treatment strip 106. To this end, each trough 114 may include a shelf 116 substantially in a center portion of the trough 114. Due to the shelf 116, each end of the trough 114 can also include a recess 118. The shelf 116 and the recess 118 work together to allow an end-user to easily access the treatment strip 106. For example, a portion of the treatment strip 106 can hang off the shelf 116 and over the recess 118, thus allowing an end-user to slide his/her finger under the portion of the treatment strip 106 that is hanging off the shelf 116. Upon positioning their finger under the treatment strip 106, the end-user can simply pull the treatment strip 106 away from the trough 114.

The trough 114 can vary in geometric dimension and configuration from one rigid tray 202 to the next, or within the same rigid tray 202. For example, FIG. 1A illustrates that the trough 114 may have a rectangular length with rounded ends. However, in alternative implementations, the geometric configuration may vary widely depending on the geometric configuration of the item to be packaged witin the package 100.

Similarly, the geometric dimensions of the trough 114 can vary from one embodiment to the next, and within the same embodiment. For example, FIG. 1A illustrates four troughs 114 all having substantially the same geometric dimensions. Attentively, however, the troughs 114 can be configured to be different sizes to hold different sized items.

As mentioned above, each trough 114 includes a shelf 116 on which the treatment strip 106 is positioned. Treatment strips 106 may have various properties and characteristics. In one embodiment, the treatments strips 106 comprise a gummy surface 108 and backing material 110. The gummy surface 108 is sticky and includes adhesive properties, while the backing surface 110 does not easily adhere to other surfaces. It is noteworthy that the treatment strip 106 is not attached to, nor does it include, a separate release liner. The treatment strips 106 can be of multiple sizes such as the molar strips (e.g., the smaller of the treatment strips 106) or the bicuspid-to-bicuspid strips (e.g., the longer of the treatment strips 106).

In one example, the treatment strip 106 is positioned on the shelf 116 of the trough 114 by placing the backing surface 110 on the shelf 116. For example, the backing surface 110 interfaces with the shelf 116 portion of the trough 114. Because the backing surface 110 does not easily adhere to other surfaces, a bead of adhesive 120 may be applied to the shelf 116 prior to positioning the treatment strip 106 within the trough 114. The adhesive 120 helps to securely hold the treatment strip 106 in place during shipping and handling of the package 100. However, the adhesive 120 has characteristics such that the adhesive 120 and backing surface 110 may be separable upon an end-user pulling the treatment strip 106 away from the shelf 116.

Although the adhesive 120 can be almost any adhesive that will releasably secure the backing material 110 of the treatment strip 106, one embodiment of the present invention calls for the use of silicon as the adhesive. Various other types of fasteners may be used to releasably hold the treatment strip 106 to the shelf 116 within the trough 114 depending on a particular implementation.

Due to the fact that the backing surface 110 of the treatment strip 106 interfaces with the shelf 116, the gummy surface 108 remains untouched by any portion of the package 100. In particular, the treatment strips 106 are placed gummy surface up. Once the treatment strips 106 are placed within the troughs 114, a cover 112 (e.g., a foil or plastic covering) completely covers the troughs and is sealed to the rigid shell 102 along the perimeter of the rigid shell 102. Cover 112 may be heat sealed, glued, chemically bonded, or simply attached to the rigid tray 102 using any variety of adhesive products and methods.

Even after being sealed to the rigid tray 102, the cover 112 does not contact the gummy surface 108 of the treatment strips 106 because the troughs 114 are configured to be deep enough that the cover 112 cannot interfere with the treatment strips 106. Thus, no part of the package 100 interacts with the gummy surface 108, leaving the gummy surface 108 (generally containing the medicament) untouched are ready for use by the end-user.

Upon delivery, the end-user removes the cover 112 and, with the end-user's fingers utilizing the recess 118 in the trough 114, the end-user grasps and peels away the treatment strip 106 from the adhesive bead 120. Because the rigid tray 202 provides a no contact surface over the gummy side 108 of the treatment strip 106, the treatment strip 106 is much easier to remove compared to other conventional packaging systems.

Figure 1B:
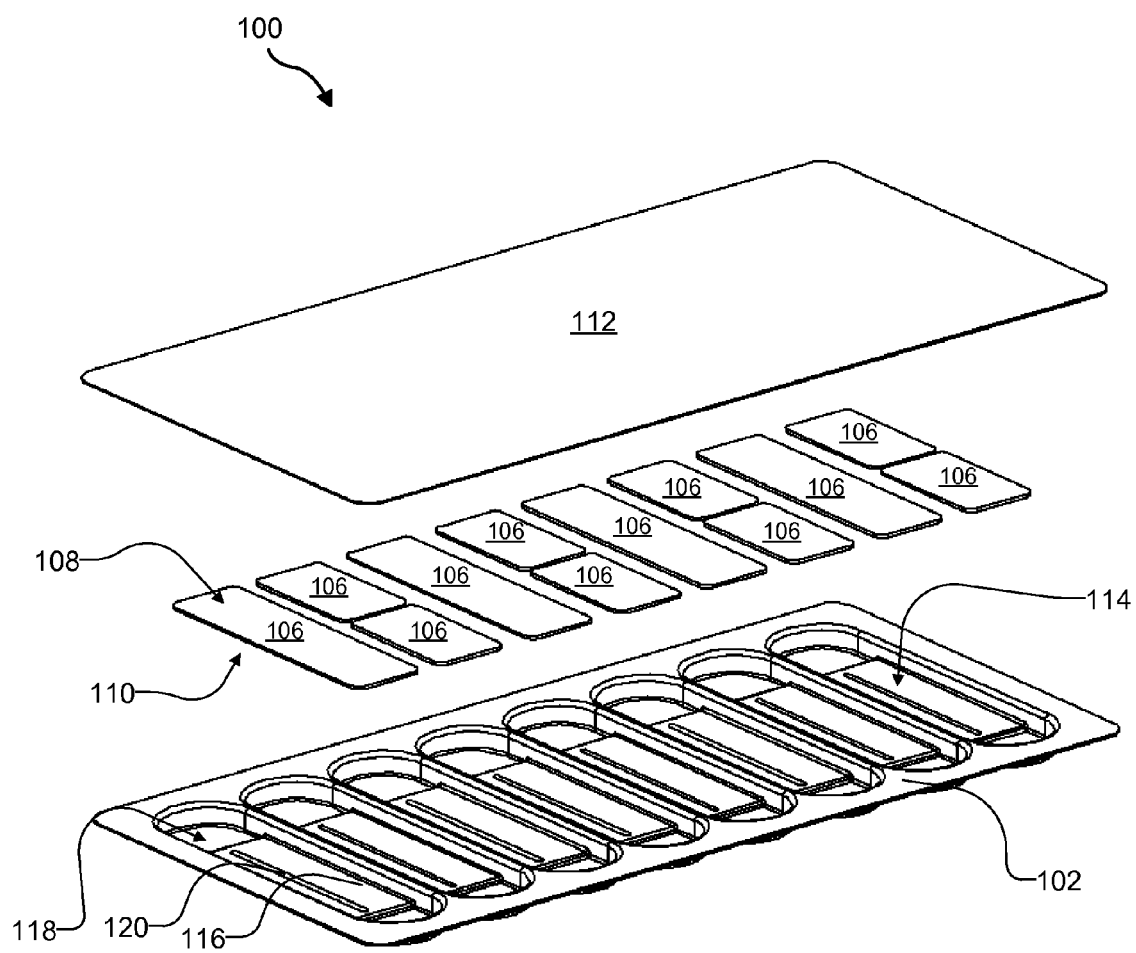
FIG. 1B illustrates an exploded view of another implementation of a package according to principles described herein.

FIG. 1A illustrates a package 100 that is configured to provide a single dose of treatment strips 106 (i.e., treatments strips for both the top and bottom teeth). On the other hand, FIG. 1B illustrates an example embodiment that is configured to provide two doses of treatment strips (i.e., two treatment strips for both the top and bottom teeth). Various other trays may be configured to provide more or fewer doses as a particular implementation requires.

Figure 2A:
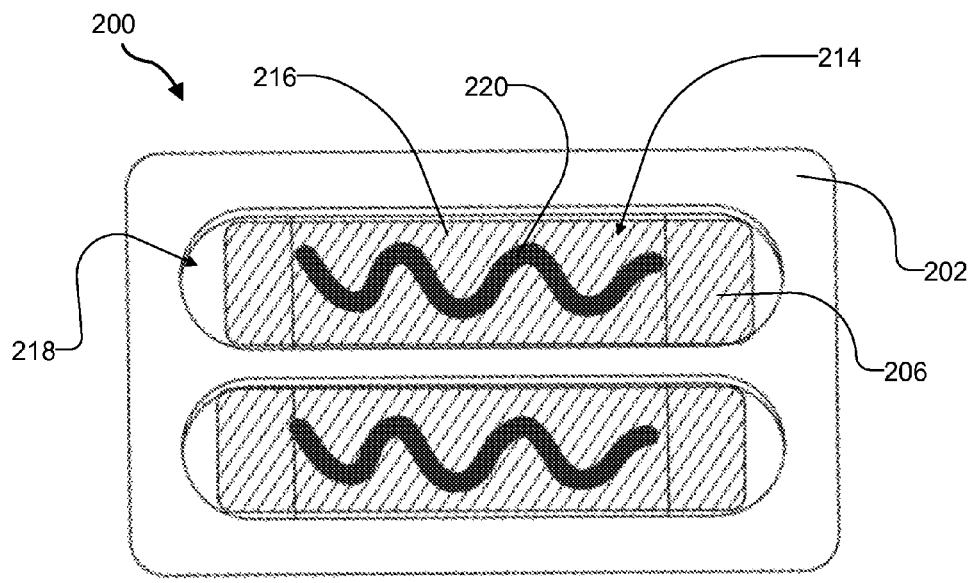
FIG. 2A illustrates top plan view of an example embodiment of a package according to principles described herein.
Figure 2B:
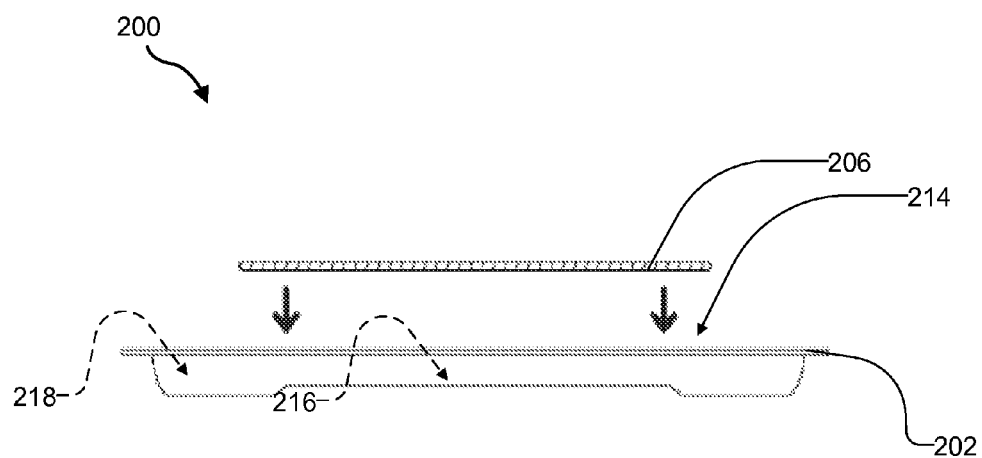
FIG. 2B illustrates a side view of the package in FIG. 2A.

For example FIGS. 2A and 2B illustrate yet another example package 200. Package 200 is similar and can include all the features discussed above with respect to FIGS. 1A and 1B. For example, package 200 includes a rigid tray 202 that includes a trough 214. The trough 214 includes a shelf 216 that forms a recess 218 to assist the end-user in accessing a treatment strip 206. As with package 100, the treatment strips 206 are positioned within the troughs with the gummy surface side up such that no part of the package 200 interfaces with the gummy surface.

Different, however from package 100, is the pattern in which the adhesive bead 120 is applied to the shelf 116. As illustrated in FIG. 2A, the adhesive bead 220 is applied in a rounded zigzag pattern. The rounded zigzag pattern can assist the adhesive bead in staying adhered to the shelf 216, while at the same time releasing the treatment strip 206 as the user is peeling back the treatment strip 206. The adhesive bead 220 can also be applied in various other patterns.

FIG. 2B shows a side view of the package 200 discussed with reference to FIG. 2A. In particular, FIG. 2B clearly illustrates the function of the shelf 216 and the recess 218 within the trough 214. As is shown, the recess 218 dips down from the shelf 216. The treatment strip 206 is sized to hang over the ends of the shelf 216 (indicated by the large arrows) such that a user can slide a finger into the recess 218 and under the treatment strip 206 without disturbing the gummy surface 208 of the treatment strip 206.

Figure 3:
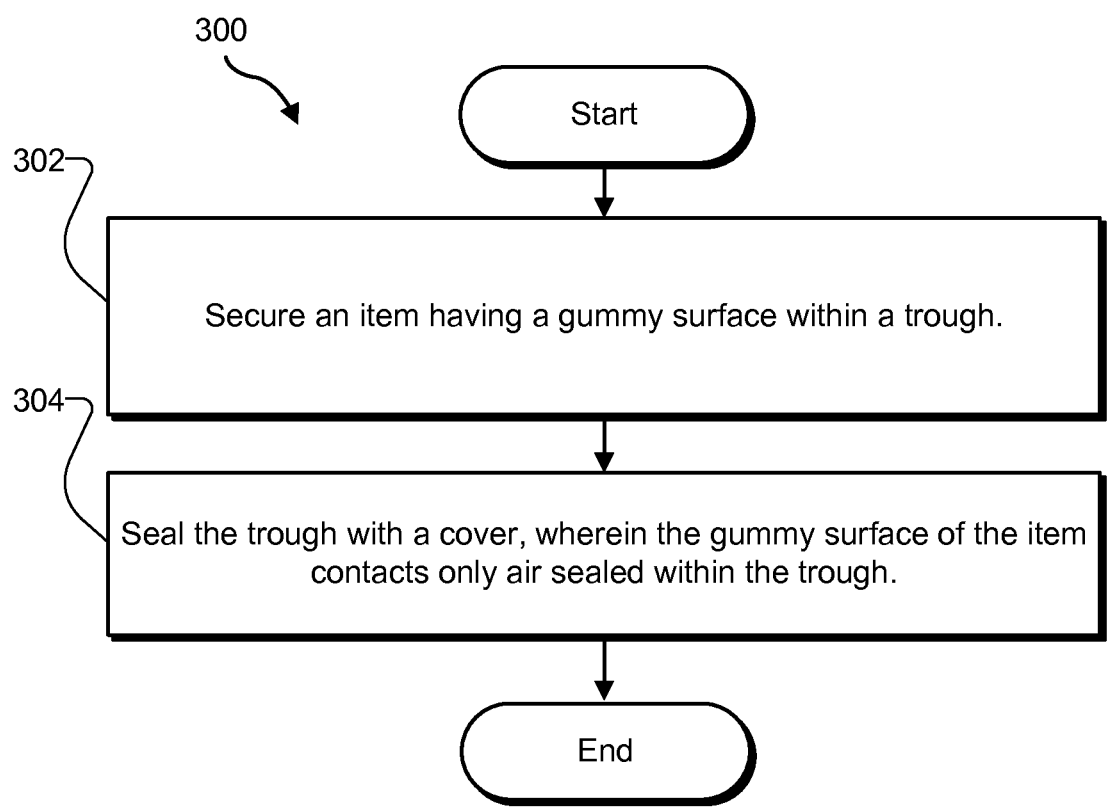
FIG. 3 illustrates an example method of packaging a gummy item according to principles described herein.

Accordingly, FIGS. 1A through 2B and the corresponding text provide a number of different components and modules that provide a package used to package an item with at least one gummy surface. In addition to the foregoing, implementations of the present invention can also be described in terms of flowcharts comprising one or more acts in a method for accomplishing a particular result. For example, FIG. 3 illustrates a method 300 of packaging an item with at least one gummy surface. The acts of FIG. 3 are discussed more fully below with respect to the components discussed with reference to FIG. 1A through FIG. 2B.

For example, FIG. 3 shows that the method 300 comprises an act 302 of securing an item having a gummy surface within a trough. For example, FIG. 2A illustrates that the treatment strip 206, which has a gummy surface 208, is secured within the trough 214.

Also, the method 300 comprises an act 304 of sealing the trough with a cover, wherein the gummy surface of the item contacts only air sealed within the trough. For example, FIG. 1A illustrates that the treatment strip 106, which as a gummy surface 108, can be sealed between the cover 112 and the trough 114 such that the gummy surface does not contact any portion of the package 100.

Accordingly, the diagrams and figures provided in FIG. 1A through FIG. 3 illustrate a number of methods, devices, systems, configurations, and components that can be used to effectively package an item having a gummy surface.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A packaged dental product, comprising:
    a rigid tray;
    a trough formed into the rigid tray;
    a shelf located in a middle portion of the trough;
    a dental product consisting of a flat dental treatment strip having a gummy surface and a backing surface opposite the gummy surface, the backing surface attached to the shelf with an adhesive; and;
    a cover that environmentally seals the flat dental treatment strip within the trough,
    wherein, the gummy surface of the flat dental treatment strip remains untouched by the rigid tray, the trough, and the cover.

2. The packaged dental product recited in claim 1, wherein the cover is sealed to the rigid tray by way of a heat seal.

3. The packaged dental product recited in claim 1, further comprising a recess adjacent to the shelf, wherein the recess is offset in height from the shelf.

4. The packaged dental product recited in claim 3, wherein the adhesive comprises an adhesive bead applied to the shelf.

5. The packaged dental product recited in claim 4, wherein the adhesive bead is applied in a rounded zigzag pattern.

6. The packaged dental product recited in claim 1, wherein the gummy surface includes an agent configured to provide a treatment to teeth upon contact.

7. A packaged dental product, comprising:
    a rigid tray;
    a plurality of troughs on the rigid tray;
    a shelf within a middle portion of the trough;
    a dental product consisting of a flat dental treatment film having a gummy surface and a backing surface opposite the gummy surface, the backing surface attached to the shelf with an adhesive;
    wherein, the gummy surface of the flat dental treatment film faces up from the trough and does not contact any part of the rigid tray.

8. The packaged dental product of claim 7, wherein the adhesive comprises an adhesive bead between the shelf and the backing surface of the flat dental treatment film.

9. The packaged dental product of claim 8, further comprising a cover that environmentally seals the flat dental treatment film within the trough.

10. The packaged dental product of claim 9, wherein the gummy surface of the flat dental treatment film contacts only air sealed between the rigid tray and the cover.

11. A method of packaging, comprising:
    forming a trough into a rigid tray;
    attaching a backing surface of a dental product consisting of a flat dental treatment strip to a shelf located in a middle portion of the trough with an adhesive;
    sealing the trough with a cover such that the flat dental treatment strip within the trough is environmentally sealed and a gummy surface of the flat dental treatment strip, opposite the backing surface of the flat dental treatment strip, remains untouched by the rigid tray, the trough, and the cover.

12. The method recited in claim 11, wherein attaching the backing surface of the flat dental treatment strip to the shelf located in the middle portion of the trough with an adhesive further comprises applying an adhesive bead between the backing surface of the flat dental treatment strip and the shelf located within the middle portion of the trough.

13. The method recited in claim 12, wherein the adhesive bead is silicon.

* * * * *